United States Patent [19]

Schmitt

[11] Patent Number: 5,707,634

[45] Date of Patent: Jan. 13, 1998

[54] FINELY DIVIDED SOLID CRYSTALLINE POWDERS VIA PRECIPITATION INTO AN ANTI-SOLVENT

[75] Inventor: William J. Schmitt, Kalamazoo, Mich.

[73] Assignee: Pharmacia & Upjohn Company, Kalamazoo, Mich.

[21] Appl. No.: 488,710

[22] Filed: Jun. 8, 1995

Related U.S. Application Data

[63] Continuation of Ser. No. 659,425, Mar. 14, 1991, abandoned, which is a continuation-in-part of Ser. No. 253,849, Oct. 5, 1988, abandoned.

[51] Int. Cl.$^6$ .................................................. A61K 9/14
[52] U.S. Cl. ............................ 424/400; 424/489; 424/69
[58] Field of Search ........................... 424/401, 489; 210/634; 435/178, 180, 182; 514/202

[56] References Cited

U.S. PATENT DOCUMENTS

| | | | |
|---|---|---|---|
| 3,981,957 | 9/1976 | van Brederode et al. | 260/878 R |
| 4,012,461 | 3/1977 | van Brederode | 260/878 R |
| 4,044,126 | 8/1977 | Cook et al. | 424/423 |
| 4,123,559 | 10/1978 | Vitzthum et al. | 426/312 |
| 4,124,607 | 11/1978 | Beaton | 260/397.25 |
| 4,192,731 | 3/1980 | Stearns et al. | 208/8 LE |

(List continued on next page.)

FOREIGN PATENT DOCUMENTS

| | | |
|---|---|---|
| 899667 | 6/1962 | European Pat. Off. . |
| 2624924 | 12/1977 | European Pat. Off. . |
| 2608988 | 7/1988 | European Pat. Off. . |
| 1525181 | 9/1978 | United Kingdom . |

OTHER PUBLICATIONS

Gallagher et al. in Supercritical Fluid Science & Technology ACS Symp. 406—Johnson & Penning et al. 1989 pp. 334–343.

Supercritical Fluid Science and Technology American Chemical Society, Washington, D.C. 1989 pp. 335–343 and 353–354.

Kirk–Othmer, "Crystallization . . . salting–out", Encyclopedia of Chemical Technology, vol. 7, 3rd. Edition, pp. 243, 261–263, (1979).

M. E. Paulaitis, et al, "Supercritical Fluid Extraction", Reviews In Chemical Engineering, vol. I, No. 2, pp. 179–250 (1983).

*Primary Examiner*—Neil S. Levy
*Attorney, Agent, or Firm*—Bruce Stein

[57] ABSTRACT

The present invention is a process for producing a finely divided solid which comprises (1) dissolving the solid to be finely divided in a liquid carrier solvent to form an injection solution and (2) adding the injection solution of step (1) to a volume of anti-solvent sufficient to precipitate or crystallize the solid.

The solid can be a pharmaceutical, agricultural chemical, commercial chemical, fine chemical, food item, photographic chemical, dye, explosive, paint, polymer or cosmetic.

26 Claims, 1 Drawing Sheet

U.S. PATENT DOCUMENTS

| | | | |
|---|---|---|---|
| 4,247,570 | 1/1981 | Zosel | 426/481 |
| 4,263,253 | 4/1981 | Pilz et al. | 422/1 |
| 4,367,178 | 1/1983 | Heigel et al. | 260/403 |
| 4,582,731 | 4/1986 | Smith | 427/421 |
| 4,737,384 | 4/1988 | Murthy et al. | 210/658 |
| 4,824,570 | 4/1989 | Bethuel et al. | 210/511 |
| 4,828,702 | 5/1989 | Coenen et al. | 210/634 |
| 4,933,334 | 6/1990 | Shimizu et al. | 514/202 |
| 4,964,995 | 10/1990 | Chum et al. | 210/634 |
| 5,041,469 | 8/1991 | Hosteter et al. | 521/189 |
| 5,043,280 | 8/1991 | Fischer et al. | 210/634 |

OTHER PUBLICATIONS

V. Krokonis, "Supercritical Fluid Nucleatiion of Difficult--to-Comminute Solids", AIChE, 1983 Annual Meeting., San Francisco, CA Nov. 25–30, 1984, Paper 140f, pp. 1–19 plus the Abstract.

K. A. Larson, et al, "Evaluation of Supercritical Fluid Extraction in the Pharmaceutical Industry", Biotech. Prog., vol. 2, No. 2, pp. 73–82, Jun. 1986.

R. C. Petersen, et al, "Rapid Precipitation of Low Vapor Pressure Solids from Supercritical Fluid Solutions: The Formation of Thin Films and Powders", J. Am. Chem. Soc., vol. 108, pp. 2100–2102 (1986).

H. Loth, et al, "Properties and dissolution of drugs micronized by crystallizations from supercritical gases", International Journal of Pharmaceutics, vol. 32, pp. 265–267 (1986).

E. Stahl, et al, "New Developments in the Field of High--Pressure Extraction of Natural Products with Dense Gases", Ber. Bunsenges. Phys. Chem., vol. 88, pp. 900–907 (1984).

Mitsu Toatsu Chemicals Co., Ltd. Chemical Abstracts, vol. 78, No. 18, 7 May 1973, (Columbus, Ohio, US), see p. 256, abstract 115234g, & JP, A, 7305918: 25 Jan. 1973.

Y. Kato et al, "Microcrystallization method for amobarbital and the pysicochemical properties of the products", Chem. Pharm. Bull., vol. 28, No. 3, March 1980 pp. 968–972.

D.W. Matson et al, "Formation of fine particles in super-critical fluid micelle systems", Chemical Abstracts, vol. 108, No. 24, 13 Jun. 1988, p. 423, abstract 210924d, & Mater. Lett. 1987, 6(1–2), 31–3.

G. Parkinson et al, article in Chem Engineering, Jul. 1989, p. 39.

American Institute of Chemical Engineers Annual Meeting on Nov. 29, 1988, (Gas Recrystallization: A new Process to Recrystallize Compounds Insoluble in Supercritical Fluids; paper No. 48c.

FINELY DIVIDED SOLID CRYSTALLINE POWDERS VIA PRECIPITATION INTO AN ANTI-SOLVENT

The present patent application is a continuation of U.S. patent application Ser. No. 07/659,425, filed 14 Mar. 1991, which is a continuation (national phase) of international application No. PCT/US89/03783, filed 6 Sep. 1989, which is a continuation-in-part of U.S. application Ser. No. 07/253,849, filed 5 Oct. 1988, abandoned.

BACKGROUND OF THE INVENTION

1. Field of the Invention

This invention relates to processes for making finely divided solid powders such as pharmaceutical and technical chemicals or explosive agents which are normally difficult to solubilize in aqueous media or to subdivide without extensive chemical or physical treatments such as micronizing or repeated grinding operations, or in the case of explosives, hazardous operations. More particularly, this invention provides a process for producing finely divided solid crystalline or amorphous powders involving the sub- or super critical gases which process is not limited by the solubility of the solid in the pure supercritical gas, per se.

2. Description of the Related Art

Adding a normally liquid anti-solvent to a liquid solution of a solid to be precipitated or subdivided, or of adding the liquid solution containing the solid to be precipitated or subdivided into the liquid anti-solvent is a well-known chemical plant practice which is often referred to as the "salting out" effect. See Kirk-Othmer's ENCYCLOPEDIA OF CHEMICAL TECHNOLOGY, Third Edition, 7, John Wiley & Son, Publishers (1979), page 261 in a chapter on "Crystallization".

Adding a solution of a solid dissolved in a good liquid solvent therefor to a comparatively large volume of poor liquid solvent is known as controlled microprecipitation and is practiced on an industrial scale for a variety of solid products.

The use of compressed supercritical gas for its solubility effect on some solids is also an old concept referred to in U.S. Pat. No. 4,263,253 (column 1), but has become of more recent interest for the production of fine powders. In their review of supercritical fluid technology, Paulaitis, M. E. et al, "Supercritical Fluid Extraction", Rev. Chem. Eng., 1 (2) (1983), pp. 179–250, describe the redistribution of particle sizes of solids via supercritical fluid nucleation. Krukonis, V. J., "Supercritical Fluid Nucleation of Difficult to Comminute Solids", Paper No. 140f, presented at the Annual Meeting of the AIChE, San Francisco, November 1984, expands upon that work.

In U.S. Pat. No. 4,582,731 there is described a process for making a finely divided solid using a supercritical fluid as a solvent for the solid to be subdivided which solution is then expanded into a low pressure vacuum atmosphere to quickly separate the depressured supercritical gas solvent from the solid. This latter work is further described in a paper by Peterson, R. C. et al, "Rapid Precipitation ... Supercritical Fluid Solutions; The Formation of Thin Films and Powders", J. Am. Chem. Soc., 108, 2100–2103 (1986). The direct application of supercritical fluid extraction to the production of pharmaceutical powders was described by Larson, K. A. et al, "Evaluation of Supercritical ... Industry", Biotech. Prog. 2 (2) (June 1986), pp. 73–82, and independently by Loth, E. et al, "Properties ... Supercritical Gases", Int. J. Pharm., 32, 265–267 (1986).

All of these literature and patent descriptions are similar insomuch as they all teach that the solid compound to be micronized or subdivided must first be dissolved in an appropriate supercritical fluid. The supercritical fluid containing the dissolved solute is then rapidly expanded (flashed) to separate the supercritical gas from the solid and to recover the dry, micronized powder.

It is also disclosed in Ber. Bunsenges, Phys. Chem., 88, 900 (1984) that complex oily, gummy or otherwise highly viscous natural products such as crude lecithin can be stripped of their more volatile components by extraction with a supercritical gas, leaving behind insoluble matter in the form of a recoverable powder (also see U.S. Pat. No. 4,367,178). This phenomenon forms the basis of all supercritical solvent leaching operations, where for example the unextracted mass may be organic matter as in the leaching of coffee (U.S. Pat. No. 4,247,570) or spice (U.S. Pat. No. 4,123,559). If coal is extracted with a mixture of supercritical xylene and tetralin then the undissolved portion is a particulate ash consisting of organic char and inorganic minerals (U.S. Pat. No. 4,192,731).

A similar but opposite process has been described in the literature, see Chemical Engineering, July 1989, p 39. The process is called the "GAS" (gas-anti-solvent) process and is performed by adding a supercritical fluid to a premixed volume of dissolved solute dissolved in an organic liquid solvent. As the supercritical fluid dissolves in the solution, the solid precipitates out. A speech describing the GAS process was given at the American Institute of Chemical Engineers Annual Meeting on Nov. 29, 1988, (Gas Recrystallization: A new Process to Recrystallize Compounds Insoluble in Supercritical Fluids; paper No. 48c).

In addition to the above the following patents may be of interest as illustrating uses or applications of the above background technology.

U.S. Pat. No. 3,981,957 discloses a process for making a high density polymer powder comprising melting a thermoplastic polymer to a melt, mixing the polymer melt with a solvent and discharging the polymer melt/solvent mixture through a nozzle in contact with a blowing gas such as nitrogen. There is no mention of the use of a supercritical solvent or a supercritical anti-solvent procedure.

U.S. Pat. No. 4,012,461 discloses a process for producing polymer powders which includes the step of atomizing a polymer slurry into a vaporization zone on the presence of a drying gas. There is no mention of the use of a supercritical gas anti-solvent procedure.

U.S. Pat. No. 4,124,607 discloses a process for getting difficult to dissolve soluble sterol starting materials into a fermentation medium by dissolving the sterol in an organic solvent with subsequent removal of the organic solvent by heat or by reduced pressure.

U.S. Pat. No. 4,263,253 discloses a process for sterilizing solids, e.g., pharmaceutical active ingredients, by dissolving the non-sterile solid in a gas under supercritical conditions, and then passing the resulting solution through a sterilizing filter to provide a sterile fluid gas/solid mixture.

These above processes are different from the process of this invention which involves adding a solution of the solute to be micronized or subdivided in a conventional liquid solvent and then adding this solution to a compressed liquified or supercritical gas atmosphere, which gas is essentially an anti-solvent or non-solvent for the solid to be micronized or subdivided as a solid. Moreover, the processes described above, with the exception of the GAS process described in Chemical Engineering in July of 1989, which involve the use of supercritical or liquified gases are limited in their application to solids which are soluble in the supercritical gas atmosphere. However, many pharmaceutical, agricultural chemicals, commercial chemicals, fine chemicals, food items, photographic chemicals, dyes, explosives, paints, polymers or cosmetics and other solid materials which need to be further subdivided are not very soluble in the common and reasonably priced supercritical gas solvents such as carbon dioxide, nitrous oxide, ethylene, fluoroform and the like.

This process invention is intended to provide a solution to the problem of treatment of solids, particularly those which are not soluble enough in a common supercritical or liquified gaseous solvent for making large quantities of solids, which must be finely subdivided for example, pharmaceuticals, agricultural chemicals, commercial chemicals, fine chemicals, food items, photographic chemicals, dyes, explosives, paints, polymers or cosmetics.

SUMMARY OF THE INVENTION

Disclosed is a process for producing a finely divided solid which comprises
(1) dissolving the solid to be finely divided in a liquid carrier solvent to form an injection solution and
(2) adding the injection solution of step (1) to a volume of anti-solvent sufficient to precipitate or crystallize the solid.

Also disclosed is a process for producing a sterile finely divided solid which comprises
(1) dissolving the solid to be finely divided in a liquid carrier solvent to form an injection solution,
(2) passing the injection solution through a sterilizing filter,
(3) passing an anti-solvent through a sterilizing filter,
(4) adding the injection solution of step (1) to a volume of anti-solvent sufficient to precipitate or crystallize the solid in a sterilized pressure vessel.

DETAILED DESCRIPTION OF THE INVENTION

Figure 1:
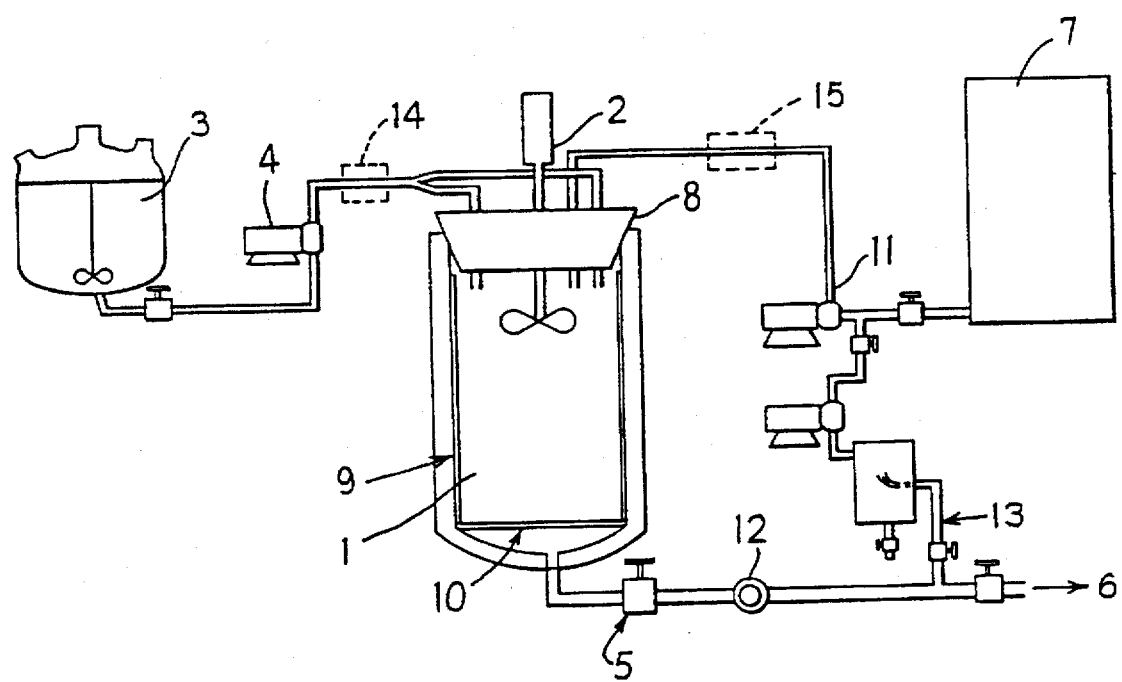
FIG. 1 is a sketch plan and block symbol view of typical apparatus which can be used to operate the process of this invention.

This invention is a process for producing a finely divided solid referred to as "microprecipitation from a compressed gas," or more simply "gas microprecipitation."

The operable solids to be finely divided in the process of the present invention include almost any solid material which needs to be sub-divided in the solid state and which can be dissolved in some liquid carrier solvent. Operable solids include for example, a pharmaceutical, agricultural chemical, commercial chemical, fine chemical, food item, photographic chemical, dye, explosive, paint, polymer or cosmetic. It is preferred that the solid be a pharmaceutical (both prescription and non-prescription drugs). It is preferred that the pharmaceutical be a steroid, benzodiazepene, penicillin, or cephalosporin. The preferred steroids are those set forth in CHART A where (A-I) $R_{10}$ is $\alpha$—$R_{10\text{-}1}$:$\beta$—$CH_3$, where $R_{10\text{-}1}$ and $R_5$ are taken together are —$CH_2$—$CH_2$—CO—CH= or —CH=CH—CO—CH=;

(A-II) $R_{10}$ and $R_5$ taken together are =CH—CH=COH—CH=;

$R_6$ is $\alpha$—$R_{6\text{-}1}$:$\beta$—H where $R_{6\text{-}1}$ is —H, —F or —$CH_3$;

$R_7$ is —H or —S—CO—$CH_3$;

$R_9$ is —H, —F, —Cl or —Br;

$R_{11}$ is =O or $\alpha$—H:$\beta$—OH;

$R_{16}$ is $\alpha$—$R_{16\text{-}1}$:$\beta$—$R_{16\text{-}2}$ where $R_{16\text{-}1}$ is —H, —OH or —$CH_3$ and where $R_{16\text{-}2}$ is —H or —$CH_3$ with the proviso that one of $R_{16\text{-}1}$ or $R_{16\text{-}2}$ is —H;

$R_{17}$ is —H, —CO—$R_{17\text{-}1}$ where $R_{17\text{-}1}$ is $C_1$–$C_5$ alkyl;

$R_{21}$ is —Cl, —OH or —O—CO—$R_{21\text{-}1}$ where $R_{21\text{-}1}$ is $C_1$–$C_3$ alkyl, with the proviso that when $R_{16\text{-}1}$ is —OH and when $R_{17}$ is —H, the two groups can form an acetonide.

Examples of pharmaceuticals include triamcinolone acetonide, triamcinolone, dexamethasone, dexamethasone sodium phosphate, methylprednisolone acetate, hydrocortisone, hydrocortisone acetate, medroxyprogesterone acetate, isoflupredone acetate, alprazolam, triazolam, penicillin, glyburide, ampicillin, ibuprofen, spectinomycin, erythromycin, flurbiprofen and their salts.

Examples of commercial chemicals include nylon, polystyrene, benzoic acid, benzene hexachloride and paraffin wax. Examples of fine chemicals includes citric acid, dichlorobenzedine and benzophenone. Examples of food items include cocoa and powdered milk. Examples of explosives include plastic explosives, trinitrotoluene (TNT) and other military munitions. Examples of agricultural chemicals include herbicides and insecticides.

The solid to be finely divided is first dissolved in a suitable liquid carrier solvent. The liquid carrier solvent is selected based on its ability to dissolve the solid to be finely divided, its miscibility with an anti-solvent, toxicity, cost and other factors. The resulting solution of solid dissolved in the liquid carrier solvent is called the injection solution.

The liquid carrier solvent is a conventional liquid solvent (at ambient conditions) in which the solid to be finely divided is quite soluble. In addition the liquid solvent must possess at least partial miscibility with the anti-solvent. Most organic solvents are at least partially miscible with most anti-solvents. Water is only slightly soluble in the anti-solvent carbon dioxide, and even less soluble in ethane, and so, while water may be used as a liquid carrier solvent, the ratio of anti-solvent to injection solution must be kept very high to prevent the formation of a water rich phase in which excessive finely divided solid solute product remains dissolved.

In general, the liquid carrier solvent is chosen for high solubility of the solid to be finely divided, miscibility with the anti-solvent being used, low toxicity, fairly high volatility, non-corrosiveness to the apparatus, and fairly low viscosity for ease of injection. It is understood that for each particular solid there are different preferred liquid carrier solvents which can be readily determined as is known to those skilled in the art. A preferred liquid carrier solvent for any particular solid to be finely divided meets the above criteria and also gives acceptable particle size, crystal form, and low residual solvent levels in the finely divided solid product, for the particular solid being microprecipitated. Suitable liquid carrier solvents include any organic solvent capable of dissolving the solute and mixtures thereof.

In general there are no preferred liquid carrier solvents because each solid has different solubility characteristics. Rather each solid will have its own preferred liquid carriers. Common liquid carrier solvents include:

alcohols of the formula $R_a$—OH where $R_a$ is $C_1$–$C_6$ alkyl or $\phi$—$CH_2$—;

ethers of the formula $R_b$—O—$R_c$ where $R_b$ and $R_c$ are the same or different and are $C_1$–$C_4$ with the proviso that the total number of carbon atoms not be more than 6, and where $R_b$ and $R_c$ can be taken together with the attached oxygen atom to form a heterocyclic ring consisting of 5-8 atoms;

ketones of the formula $R_d$—CO—$R_e$ where $R_d$ and $R_e$ are the same or different and are —H or $C_1$-$C_4$ alkyl with the provisos that (1) $R_d$ and $R_e$ can not both be —H and (2) that the total number of carbon atoms not be more than 6;

amides of the formula $R_f$—CO—NR$_g$R$_h$ where $R_f$ is —H, —CH$_3$ or —C$_2$H$_5$ and $R_g$ and $R_h$ are the same or different and are —H, —CH$_3$ or —C$_2$H$_5$ with the proviso that only one of $R_g$ or $R_h$ can be —H when $R_f$ is —CH$_3$ or —C$_2$H$_5$;

esters of the formula $R_i$—CO—O—$R_j$ where $R_i$ is $C_1$-$C_4$ alkyl and $R_j$ is —H or $C_1$-$C_4$ alkyl;

aromatic compounds such as benzene optionally substituted with 1 or 2 —Cl or with 1 or 2 —CH$_3$;

methane type compounds of the formula $C(R_k)_4$ where $R_k$ are the same or different and are —H or —Cl;

ethane optionally substituted with 1–3 —Cl;

ethene optionally substituted with 1–3 —Cl;

hydrocarbons of the formula (CH$_3$—(CH$_2$)$_{n1}$—CH$_3$ where $n_1$ is 2–6 optionally substituted with 1–4 —Cl; freons; CH$_3$—CN, glyme and mixtures thereof. Specific liquid carrier solvents include methanol, ethanol, n- and iso-propanol, n-, sec- and tert-butanol, pentanols, hexanols, heptanols, benzyl alcohol, THF, diethyl ether, methyl-tert-butyl ether, formamide, DMF, N,N-dimethylacetamide, acetone, methylethyl ketone, pentane, hexane, heptane, octane, cyclopentane, benzene, toluene, xylene, pyridine, methylene chloride, chloroform, carbon tetrachloride, chloromethane, ethylene dichloride, butyl chloride, trichloroethylene, 1,1, 2-trichlorotrifluoroethanedioxane, chlorobenzene, ethyl acetate, butyl acetate, acetonitrile, glyme, and mixtures thereof.

The anti-solvent to be used is selected based on several factors of which one of the most important is a low solubility of the pure solid to be finely divided in the anti-solvent and a high solubility of the liquid carrier solvent in the anti-solvent. The selected anti-solvent is chosen to minimize cost, maximize product yield, minimize toxicity and on other experimental aspects such as producing the correct crystal form and being easily removed from the crystalline solid, and its being the optimum non-solvent for the solid being finely divided. The selected anti-solvent is one which is at least partially, preferably completely, miscible with the carrier liquid solvent over the range of pressure and temperature encountered during the operation of the process.

Anti-solvent refers to a gas existing at a temperature equal to or above the pure gas critical temperature and at a pressure equal to or above the pure gas critical pressure. Therefore, the term anti-solvent includes supercritical fluids, compressed liquified gases and dense vapors. Because the anti-solvent is chosen which exhibits a small equilibrium solubility for the solid to be microprecipitated, the anti-solvent is an non-solvent in the process. Since the solubility of any solid compound in a anti-solvent is a function of both the temperature and pressure of the supercritical fluid ($T \geq T_c$ and $P \geq P_c$), then optimum yields of finely divided solid may be obtained by adjusting either the temperature or the pressure of the anti-solvent. It is known that lower fluid temperatures favor lower solute solubility. Thus, the process may be run with good results if the temperature of the anti-solvent is less than the critical temperature of the anti-solvent but the pressure is greater than the corresponding vapor pressure of the gas at the selected operating temperature. Under these conditions the supercritical fluid is called a compressed liquified gas, also sometimes referred to as a near-critical liquid (about $0.8\ T_c < T < T_c$ and $P > P^{vap}$). Thermodynamically this criteria is the liquid state. Further, the process also works, though generally not as well, if the anti-solvent is in the dense vapor phase ($T < T_c$ and $P < P_c$), but, for example, injecting the injection solvent into a low pressure vapor ($T < T_c$) or a low pressure gas ($T > T_c$) does not produce satisfactory finely divided solid because the anti-solvent is not capable of rapidly diffusing into the stream of impringent injection solvent and therefore not capable of rapidly solubilizing the liquid carrier solvent.

Anti-solvents include supercritical fluids, compressed liquified gases and dense vapors.

Operable anti-solvents include carbon dioxide, ethane, ethylene, nitrous oxide, fluoroform (CHF$_3$), dimethyl ether, propane, butane, isobutanes, propylene, chlorotrifluoromethane (CClF$_3$), sulfur hexafluoride (SF$_6$), bromotrifluoromethane (CBrF$_3$), chlorodifluoromethane (CHClF$_2$), hexafluoroethane, carbon tetrafluoride and mixtures thereof.

Preferred anti-solvents include carbon dioxide, ethane, ethylene and CClF$_3$; more preferred is carbon dioxide.

The solid to be finely divided is dissolved in the liquid carrier solvent to form an injection solution which is usually comprised of a slightly less than saturated concentration of the solid in the liquid carrier solvent at the temperature which injection solution is to be maintained. This temperature is usually chosen as ambient temperature (20°–25°) for reasons of operating convenience, but the injection solution can be prepared and maintained at higher or lower than ambient temperature if so desired. Reasons to use other than ambient temperature include the higher solubility loading of the solid in the liquid carrier solvent at higher or lower temperatures, thus improving the rate of finely divided solid product formation, or that the injection solvent temperature influences the particle size, crystal form or habit, residual solvent content, or other physical property of the ultimately produced finely divided solid. Although the liquid carrier solvent may be saturated with solid (now solute), it is generally preferable to inject slightly less than saturated injection solutions as this condition minimizes the plugging of porous filters, check valves, and other process equipment through which the injection solution flows prior to being injected into the anti-solvent.

The injection solution is then added to a comparatively large volume of the anti-solvent which is under the process conditions a supercritical fluid, liquified compressed gas or dense vapor. In the usual method of operation the injection solution is pumped into a stirred autoclave containing the compressed anti-solvent. When the injection solution (liquid carrier solvent containing dissolved solid) contacts the anti-solvent, the injection solution is rapidly permeated with the anti-solvent by the normal process of binary diffusion. Since the solubility of the solid is much lower in the anti-solvent than it is in the liquid carrier solvent, the dissolved solid precipitates from the anti-solvent liquid carrier solvent mixture soon after the contacting is made. Because the contacting, mixing, and diffusion occur on a fast time scale, the solid precipitates out of the mixture as small, fine particles. If contacting were made slower (such as might be achieved by slowly adding anti-solvent to a prescribed volume of liquid carrier solvent/dissolved solute solution), then larger sized particles of precipitated solid would be expected to form because of the increased time of good solubility available for kinetically controlled crystal growth.

Slow crystallizations generally produce larger crystals than rapid precipitations.

After a desired quantity of injection solvent has been added to the anti-solvent, the precipitated finely divided solid (product), must be separated from the pressured anti-solvent raffinate. This raffinate is a homogeneous mixture of mostly anti-solvent containing typically 2–10 wt % liquid carrier solvent. Thus, it is important that the liquid carrier solvent be miscible with the anti-solvent at all operating temperatures and pressures encountered in the processing while the raffinate is still in contact with the finely divided solid product. If a temperature, pressure, or composition is reached which causes a liquid carrier solvent-rich second phase to form in the raffinate, finely divided solid product may selectively redissolve in this phase and not be recoverable in a finely divided solid state. Two phase gas or liquid formation (a third phase is the solid phase) may be tolerated in the mixture if the finely divided solid is still only sparingly soluble in both phases.

Collection of the finely divided solid product is expediently performed by screening the solid in a sieve filtration operation. The anti-solvent/liquid carrier solvent/finely divided solid precipitate mixture is forced to flow through a fine porosity basket filter located at the bottom of the precipitation chamber while still under full operating pressure. The finely divided solid product is retained by the basket filter while the anti-solvent raffinate passes easily through the bed of collected solid and the sieve filter before being bled from the bottom of the precipitation chamber as clarified filtrate. The low viscosity and low surface tension of the anti-solvent is particularly amenable to fast filtration rates through a packed bed of small particles as opposed to the filtration rate of conventional liquid solvents with their inherently higher viscosities and surface tension effects. In this filtration respect supercritical fluid microprecipitation offers the advantage of rapid filtration rate usually not observed in conventional liquid microprecipitation, particularly when water is used as the conventional anti-solvent as is common practice.

It is preferred to practice the process of the present invention in a continuous processing mode. In this case the anti-solvent and injection solution are forced into the precipitation chamber and filtered raffinate exits the chamber from the down-stream side of the basket filtration device at such a regulated rate that the chamber pressure remains essentially constant with time. When sufficient solid solute dissolved in the liquid carrier solvent has been added such that the filtration basket is known to be full of product solid, then the inlet flow of injection solution is temporarily halted while pure anti-solvent continues to flow into and out of the precipitation chamber at the operating pressure so as to flush the precipitation chamber of anti-solvent containing miscible carrier solvent. After a few residence volumes of pure anti-solvent are forced through the chamber, the anti-solvent inlet is shut off while the down stream venting of anti-solvent continues. This operation reduces the chamber pressure to ambient pressure so that the chamber may be opened and the filtration basket containing finely divided product solid removed. A thoroughly dry, free flowing finely divided solid product is obtained. The application of vacuum to the precipitation chamber before opening it may facilitate the complete removal (degassing) of residual anti-solvent, and/or residual liquid carrier solvent from the finely divided solid product. Flowing low pressure nitrogen or other inert gas through the depressurized chamber before opening also facilitates the complete removal of the anti-solvent which may be adsorbed on the product solid.

In a batch microprecipitation operation, where no exit stream from the down-stream side of the filtration basket is provided, other factors may influence the logical end of the microprecipitation process besides the complete filling of the product collection basket. The batch operation is typically limited by the fact that as the liquid carrier solvent accumulates in the precipitation chamber, the solubility of the finely divided solid product also increases in the liquid carrier solvent/anti-solvent mixture, up to a point where a significant amount of desired product would be soluble in the raffinate and therefore not collected in the filtration basket assembly. Further, as injection solution is continuously forced into the precipitation chamber to effect a batch microprecipitation, The pressure in the chamber continuously increases which may require termination of the batch operation so that maximum allowable pressure operating limits on the equipment are not exceeded.

Other reasonable methods of depressurizing and collecting the finely divided product solid can be envisioned in either the batch or continuous process operations, and as such do not limit the scope of this invention as the primary process effect is that contacting a solid dissolved in a good liquid carrier solvent with an anti-solvent produces an isolatable finely divided solid product which possesses useful and advantageous properties. One such alternative collection scheme would be to not collect the solid product in a sieve filter basket within the mixing and precipitation chamber, but to have the microprecipitated product/anti-solvent slurry pass through an exit channel which branches into two separate filtration/collection devices such that, with proper valving arrangement, one collection basket device can be depressurized and emptied while the other is collecting the continuously precipitating product solid. In this way intermittent suspension of the mixing and precipitation operation would not have to occur in the mixing chamber to effect emptying the collected product, and a truly continuous anti-solvent microprecipitation process could be performed.

Operable conditions are where the solid is dissolved in the liquid carrier solvent to the extent of about 1 to about 100% of saturation for that solid in the particular liquid carrier solvent; preferred is from about 50 to about 95%, more preferred is from about 70 to about 95%.

Optionally, if desired, the process can be operated under sterile conditions to produce a finely divided sterile crystalline or powdered product by the use of a sterilizing filter (such as a 0.2 micron average pore size filter) apparatus in the lines leading to the autoclave (1). For example, the dissolved solute/carrier solvent solution can be filtration sterilized by passing that solution from the solution feed tank (3) through a sterilizing filter (14) and passing the compressed liquified or supercritical gas from gas storage tank (7) through a sterilizing filter (15) prior to mixing of the respective component solution and gas streams in a sterilized pressure vessel (1).

DEFINITIONS AND CONVENTIONS

The definitions and explanations below are for the terms as used throughout this entire document including both the specification and the claims.

DEFINITIONS

All temperatures are in degrees Centigrade.
THF refers to tetrahydrofuran.
DMF refers to dimethylformamide.
$CO_2$ refers to carbon dioxide.
Raffinate refers to the solution or mixture formed containing the liquid carrier solvent dissolved in the anti-solvent with little or no dissolved solid (solute).

Pharmaceutical refers to and includes both prescription and non-prescription drugs.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

| Term | P, T Conditions | Precise Thermodynamic State |
|---|---|---|
| Supercritical fluid | $T \geq T_c$ & $P \geq P_c$ | fluid |
| Compressed liquified gas | $T < T_c$ & $P > P^{vap}$ | liquid |
| Dense vapor | $T < T_c$ & $P < P^{vap}$ | gas (vapor) |

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

Batch Crystallization

A solution of triamcinolone acetonide (6.5 g) in THF (140 ml) is prepared.

Independently and referring to FIG. 1, the 2-liter autoclave (1) is filled with carbon dioxide at 24° and, by means of the diaphragm compressor, the liquid in the autoclave is compressed to 100 bar. The stirring element (2) is then turned on (power source not shown). The 50 ml vessel (3) is filled with the THF/triamcinolone acetonide solution. At time 0, the high pressure metering pump is turned on which begins to deliver the THF/steroid solution into the agitated carbon dioxide at a flow rate of 7 ml/min. After 5½ minutes 39 ml of THF/steroid solution is delivered and the metering pump is turned off momentarily. The addition vessel is refilled with more THF/steroid solution and the metering pump is turned back on. After 12½ minutes, the addition vessel is again nearly empty, so the metering pump was turned off. A total of 4.0 g of triamcinolone acetonide is delivered to the autoclave. The pressure in the autoclave (1) is released by slowly venting the contained carbon dioxide/THF high pressure liquid mixture through the bottom valve (5) of the autoclave (the flashed gas was vented to the atmosphere). A wash is then applied to the crystals by refilling the autoclave with liquid carbon dioxide and pressurizing the vessel to 60 bar, stirring for 10 minutes, then releasing the pressure out of the bottom valve (5). The agitator (2) is then turned off. Again carbon dioxide is vented thru the bottom valve (5). The top (8) of the autoclave is then removed and the filter basket (9) taken out. About 1 gram of fine, white powder adheres to the sides of the filter basket and covering most of the bottom 10 micron filter plate (10) in a thin layer.

Upon examination of the powder with a calibrated light microscope, it is found that most of the individual particles are of a size less than 10 microns with a few being as large as 20–30 microns.

EXAMPLE 2

Continuous Microprecipitation

This is the preferred mode of operation. Significantly more product can be made per lot.

A less than saturated injection solution is prepared by dissolving triamcinolone acetonide (8.0 g) in THF (250 ml) at 20°–25°. The autoclave (1) with filtration basket in place is then pressurized with $CO_2$ by means of compressor (11) to 110 bar and heated to 49° while stirring at 2200 RPM. The addition vessel (3) is filled with the triamcinolone acetonide/THF injection solution (250 ml). The bottom valve (5) on the autoclave is then opened and $CO_2$ is allowed to enter and to vent from the bottom while keeping the autoclave pressure constant at 110–111 bar by means of the back-pressure regulator (12).

With the pure carbon dioxide flowing at a steady state rate of about 30 g/min, the high pressure metering pump (4) is turned on thus forcing the 20°–25° THF/triamcinolone acetonide injection solution into the autoclave (1) at a constant rate of 6.8 ml/min. The injection is continued for 34 minutes until about 230 ml of injection solution is added to continuously flowing carbon dioxide (0.90 kg). The injection solution addition is then stopped, but about 0.2 kg of pure carbon dioxide at 49° and 110 bar is allowed to flow through the autoclave chamber and collected solid product to purge the chamber of residual THF.

The carbon dioxide inlet is then shut off but the carbon dioxide venting is continued from the bottom of the autoclave until the pressure is reduced to ambient pressure. The autoclave is opened and the basket filter assembly is removed. The collection chamber contains triamcinolone acetonide as a fine white dry powder (7.05 g) which corresponds to an 88 wt % recovery. The average particle size of the microprecipitated product is about 5–10 microns by calibrated light microscopy.

CHART A

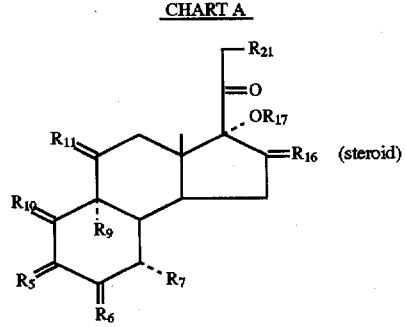

I claim:

1. A process for producing a non-sterile freely divided solid of less than or equal to 30 microns selected from the group consisting of a pharmaceutical, agricultural chemical, commercial chemical, free chemical, food item, photographic chemical, dye, explosive, polymer or cosmetic which comprises:

(1) dissolving the solid to be finely divided in a liquid carrier solvent to form an injection solution and (2) adding the injection solution of step (1) to a volume of anti-solvent sufficient to precipitate or crystallize the solid, where the anti-solvent is selected from the group consisting of carbon dioxide, ethane, ethylene, nitrous oxide, fluoroform ($CHF_3$), dimethyl ether, propane, butane, isobutanes, propylene, chlorotrifluormethane ($CClF_3$), sulfur hexafluoride ($SF_6$), bromotrifluoromethane ($CBrF_3$), chlorodifluoromethane ($CHClF_2$), hexafluoroethane, carbon tetrafluoride and mixtures thereof where the finely divided solid is of substantially the same purity as was the pharmaceutical, agricultural chemical, commercial chemical, fine chemical, food item, photographic chemical, dye, explosive, polymer or cosmetic starting material.

2. A process for producing a finely divided non-sterile solid according to claim 1 where the solid is a pharmaceutical.

3. A process for producing a finely divided non-sterile solid according to claim 2 where the pharmaceutical is asteroid, benzodiazepene, penicillin, or cephalosporin.

4. A process for producing a finely divided non-sterile solid according to claim 3 where the pharmaceutical is asteroid of the formula

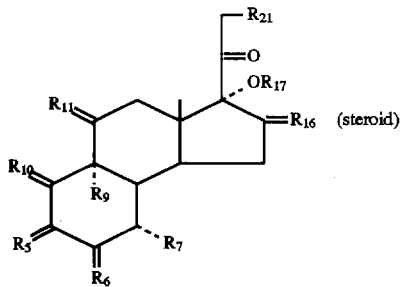 (steroid)

where (A-I) $R_{10}$ is $\alpha$—$R_{10\text{-}1}$:$\beta$—$CH_3$, where $R_{10\text{-}1}$ and $R_5$ are taken together are —$CH_2$—$CH_2$—$CO$—$CH=$ or —$CH=CH$—$CO$—$CH=$;

(A-II) $R_{10}$ and $R_5$ taken together are $=CH$—$CH=COH$—$CH=$;

$R_6$ is $\alpha$—$R_{6\text{-}1}$:$\beta$—H where $R_{6\text{-}1}$ is —H, —F or —$CH_3$;

$R_7$ is —H or —S—CO—$CH_3$;

$R_9$ is —H, —F, —Cl or —Br;

$R_{11}$ is $=O$ or $\alpha$—H:$\beta$—OH;

$R_{16}$ is $\alpha$—$R_{16\text{-}1}$:$\beta$—$R_{16\text{-}2}$ where $R_{16\text{-}1}$ is —H, —OH or —$CH_3$ and where $R_{16\text{-}2}$ is —H or —$CH_3$ with the proviso that one of $R_{16\text{-}1}$ or $R_{16\text{-}2}$ is —H;

$R_{17}$ is —H, —CO—$R_{17\text{-}1}$ where $R_{17\text{-}1}$ is $C_1$-$C_5$ alkyl;

$R_{21}$ is —Cl, —OH or —O—CO—$R_{21\text{-}1}$ where $R_{21\text{-}1}$ is $C_1$-$C_3$ alkyl, with the proviso that when $R_{16\text{-}1}$ is —OH and when $R_{17}$ is —H, the two groups can form an acetonide.

5. A process for producing a finely divided non-sterile solid according to claim 2 where the pharmaceutical is selected from the group consisting of triamcinolone acetonide, triamcinolone, dexamethasone, dexamethasone sodium phosphate, methylprednisolone acetate, hydrocortisone, hydrocortisone acetate, medroxyprogesterone acetate, isoflupredone acetate, alprazolam, triazolam, penicillin, glyburide, ampicillin, ibuprofen, spectinomycin, erythromycin, flurbiprofen and their salts.

6. A process for producing a finely divided non-sterile solid according to claim 1 where the liquid carrier solvent is any organic solvent capable of dissolving the solute and mixtures thereof.

7. A process for producing a freely divided non-sterile solid according to claim 6 where the liquid carrier solvent is selected from the group consisting of $R_a$—OH where $R_a$ is $C_1$-$C_6$ alkyl or $\phi$—$CH_2$—;

$R_b$—O—$R_c$ where $R_b$ and $R_c$ are the same or different and are $C_1$-$C_4$ with the proviso that the total number of carbon atoms not be more than 6, and where $R_b$ and $R_c$ can be taken together with the attached oxygen atom to form a heterocyclic ring consisting of 5–8 atoms;

$R_d$—CO—$R_e$ where $R_d$ and $R_e$ are the same or different and are —H or $C_1$-$C_4$ alkyl with the provisos that (1) $R_d$ and $R_e$ can not both be —H and (2) that the total number of carbon atoms not be more than 6;

$R_f$—CO—$NR_gR_h$ where $R_f$ is —H, —$CH_3$ or —$C_2H_5$ and $R_g$ and $R_h$ are the same or different and are —H, —$CH_3$ or —$C_2H_5$ with the proviso that only one of $R_g$ or $R_h$ can be —H when $R_f$ is —$CH_3$ or —$C_2H_5$;

$R_i$—CO—O—$R_j$ where $R_i$ is $C_1$-$C_4$ alkyl and $R_j$ is —H or $C_1$-$C_4$ alkyl;

benzene optionally substituted with 1 or 2 —Cl or with 1 or 2 —$CH_3$;

$C(R_k)_4$ where $R_k$ are the same or different and are —H or —Cl;

ethane optionally substituted with 1–3 —Cl;

ethene optionally substituted with 1–3 —Cl;

($CH_3$—($CH_2$)$_{n1}$—$CH_3$ where $n_1$ is 2–6 optionally substituted with 1–4 —Cl;

freons;

$CH_3$—CN, glyme and mixtures thereof.

8. A process for producing a finely divided non-sterile solid according to claim 7 where the liquid carrier solvent is selected from the group consisting of methanol, ethanol, n- and isopropanol, n-, sec- and tert-butanol, pentanols, hexanols, heptanols, benzyl alcohol, THF, diethyl ether, methyl-tert-butyl ether, formamide, DMF, N,N-dimethylacetamide, acetone, methylethyl ketone, pentane, hexane, heptane, octane, cyclopentane, benzene, toluene, xylene, pyridine, methylene chloride, chloroform, carbon tetrachloride, chloromethane, ethylene dichloride, butyl chloride, trichloroethylene, 1,1,2-trichlorotrifluoroethanedioxane, chlorobenzene, ethyl acetate, butyl acetate, acetonitrile, glyme, and mixtures thereof.

9. A process for producing a finely divided non-sterile solid according to claim 1 where the solid is dissolved in the liquid carrier solvent to the point of about 1 to about 100 weight percent of saturation for that solid in the particular liquid carrier solvent.

10. A process for producing a finely divided non-sterile solid according to claim 1 where the liquid carrier solvent is completely miscible with the anti-solvent.

11. A process for producing a finely divided non-sterile solid according to claim 1 where the injection solution is added continuously to the anti-solvent and the finely divided solid is collected in a continuous manner.

12. A process for producing a freely divided non-sterile solid according to claim 1 where the injection solution is added to the anti-solvent and the finely divided solid is collected in a batch manner.

13. A process for producing a finely divided non-sterile solid according to claim 1 where the collection of the finely divided solid is aided by the application of heat, vacuum, forced low pressure inert gas or a combination thereof.

14. A process for producing a finely divided sterile solid of less than or equal to 30 microns selected from the group consisting of a pharmaceutical, agricultural chemical, commercial chemical, free chemical, food item, photographic chemical, dye, explosive, polymer or cosmetic which comprises:

(1) dissolving the solid to be finely divided in a liquid carrier solvent to form an injection solution, (2) passing the injection solution through a sterilizing filter, (3) passing an anti-solvent through a sterilizing filter; where the anti-solvent is selected from the group consisting of carbon dioxide, ethane, ethylene, nitrous oxide, fluoroform ($CHF_3$), dimethyl ether, propane, butane, isobutanes, propylene, chlorotrifluormethane ($CClF_3$), sulfur hexafluoride ($SF_6$), bromotrifluoromethane ($CBrF_3$), chlorodifluoromethane ($CHClF_2$), hexafluoroethane, carbon tetrafluoride and mixtures thereof, (4) adding the injection solution of step (2) to a volume of anti-solvent of step (3) sufficient to precipitate or crystallize the solid in a sterilized pressure vessel, where the finely divided solid is of substantially the same purity as was the pharmaceutical, agricultural chemical, commercial chemical, free chemical, food item, photographic chemical, dye, explosive, polymer or cosmetic starting material.

15. A process for producing a freely divided sterile solid according to claim 14 where the solid is a pharmaceutical.

16. A process for producing a finely divided sterile solid according to claim 15 where the pharmaceutical is asteroid, benzodiazepene, penicillin, or cephalosporin.

17. A process for producing a finely divided sterile solid according to claim 16 where the pharmaceutical is asteroid of the formula

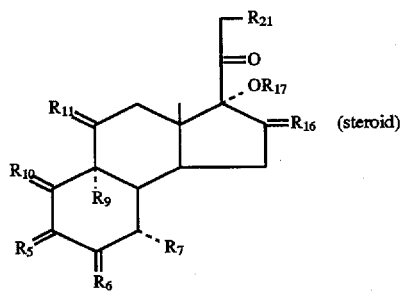

where (A-I) $R_{10}$ is $\alpha$—$R_{10-1}$:$\beta$—$CH_3$, where $R_{10-1}$ and $R_5$ are taken together are —$CH_2$—$CH_2$—$CO$—$CH$= or —$CH$=$CH$—$CO$—$CH$=;

(A-II) $R_{10}$ and $R_5$ taken together are =$CH$—$CH$=$COH$—$CH$=;

$R_6$ is $\alpha$—$R_{6-1}$:$\beta$—$H$ where $R_{6-1}$ is —$H$, —$F$ or —$CH_3$;

$R_7$ is —$H$ or —$S$—$CO$—$CH_3$;

$R_9$ is —$H$, —$F$, —$Cl$ or —$Br$;

$R_{11}$ is =$O$ or $\alpha$—$H$:$\beta$—$OH$;

$R_{16}$ is $\alpha$—$R_{16-1}$:$\beta$—$R_{16-2}$ where $R_{16-1}$ is —$H$, —$OH$ or —$CH_3$ and where $R_{16-2}$ is —$H$ or —$CH_3$ with the proviso that one of $R_{16-1}$ or $R_{16-2}$ is —$H$;

$R_{17}$ is —$H$, —$CO$—$R_{17-1}$ where $R_{17-1}$ is $C_1$-$C_5$ alkyl;

$R_{21}$ is —$Cl$, —$OH$ or —$O$—$CO$—$R_{21-1}$ where $R_{21-1}$ is $C_1$-$C_3$ alkyl, with the proviso that when $R_{16-1}$ is —$OH$ and when $R_{17}$ is —$H$, the two groups can form an acetonide.

18. A process for producing a finely divided non-sterile solid according to claim 16 where the pharmaceutical is selected from the group consisting of triamcinolone acetonide, triamcinolone, dexamethasone, dexamethasone sodium phosphate, methylprednisolone acetate, hydrocortisone, hydrocortisone acetate, medroxyprogesterone acetate, isoflupredone acetate, alprazolam, triazolam, penicillin, glyburide, ampicillin, ibuprofen, spectinomycin, erythromycin, flurbiprofen and their salts.

19. A process for producing a finely divided sterile solid according to claim 14 where the liquid carrier solvent is any organic solvent capable of dissolving the solute and mixtures thereof.

20. A process for producing a freely divided sterile solid according to claim 19 where the liquid carrier solvent is selected from the group consisting of $R_a$—OH where $R_a$ is $C_1$-$C_6$ alkyl or $\phi$—$CH_2$—;

$R_b$—O—$R_c$ where $R_b$ and $R_c$ are the same or different and are $C_1$-$C_4$ with the proviso that the total number of carbon atoms not be more than 6, and where $R_b$ and $R_c$ can be taken together with the attached oxygen atom to form a heterocyclic ring consisting of 5–8 atoms;

$R_d$—CO—$R_e$ where $R_d$ and $R_e$ are the same or different and are —$H$ or $C_1$-$C_4$ alkyl with the provisos that (1) $R_d$ and $R_e$ can not both be —$H$ and (2) that the total number of carbon atoms not be more than 6;

$R_f$—CO—$NR_gR_h$ where $R_f$ is —$H$, —$CH_3$ or —$C_2H_5$ and $R_g$ and $R_h$ are the same or different and are —$H$, —$CH_3$ or —$C_2H_5$ with the proviso that only one of $R_g$ or $R_h$ can be —$H$ when $R_f$ is —$CH_3$ or —$C_2H_5$;

$R_i$—CO—O—$R_j$ where $R_i$ is $C_1$-$C_4$ alkyl and $R_j$ is —$H$ or $C_1$-$C_4$ alkyl;

benzene optionally substituted with 1 or 2 —$Cl$ or with 1 or 2 —$CH_3$;

$C(R_k)_4$ where $R_k$ are the same or different and are —$H$ or —$Cl$;

ethane optionally substituted with 1–3 —$Cl$;

ethene optionally substituted with 1–3 —$Cl$;

($CH_3$—($CH_2$)$_{n1}$—$CH_3$ where $n_1$ is 2–6 optionally substituted with 1–4 —$Cl$;

freons;

$CH_3$—CN, glyme and mixtures thereof.

21. A process for producing a finely divided sterile solid according to claim 20 where the liquid carrier solvent is selected from the group consisting of methanol, ethanol, n- and isopropanol, n-, sec- and tert-butanol, pentanols, hexanols, heptanols, benzyl alcohol, THF, diethyl ether, methyl-tert-butyl ether, formamide, DMF, N,N-dimethylacetamide, acetone, methylethyl ketone, pentane, hexane, heptane, octane, cyclopentane, benzene, toluene, xylene, pyridine, methylene chloride, chloroform, carbon tetrachloride, chloromethane, ethylene dichloride, butyl chloride, trichloroethylene, 1,1,2-trichlorotrifluoroethanedioxane, chlorobenzene, ethyl acetate, butyl acetate, acetonitrile, glyme, and mixtures thereof.

22. A process for producing a finely divided sterile solid according to claim 14 where the solid is dissolved in the liquid carrier solvent to the point of about 1 to about 100 weight percent of saturation for that solid in the particular liquid carrier solvent.

23. A process for producing a freely divided sterile solid according to claim 14 where the liquid carrier solvent is completely miscible with the anti-solvent.

24. A process for producing a finely divided sterile solid according to claim 14 where the injection solution is added continuously to the anti-solvent and the finely divided solid is collected in a continuous manner.

25. A process for producing a finely divided sterile solid according to claim 14 where the injection solution is added to the anti-solvent and the finely divided solid is collected in a batch manner.

26. A process for producing a finely divided sterile solid according to claim 14 where the collection of the finely divided solid is aided by the application of heat, vacuum, forced low pressure inert gas or a combination thereof.

* * * * *